US00PP09546P

United States Patent [19]

Winchel

[11] Patent Number: Plant 9,546

[45] Date of Patent: May 14, 1996

[54] HYBRID TEA ROSE PLANT NAMED 'DR. BOB HARVEY'

[76] Inventor: Joseph F. Winchel, 1605 Oak Horne Dr., Harbor City, Calif. 90710

[21] Appl. No.: 192,658

[22] Filed: Feb. 7, 1994

[51] Int. Cl.[6] ..... A01H 5/00

[52] U.S. Cl. ..... Plt./18

[58] Field of Search ..... Plt./11, 18

[56] References Cited

U.S. PATENT DOCUMENTS

P.P. 6,861 6/1989 Christensen ..... Plt/11

*Primary Examiner*—Howard J. Locker

[57] ABSTRACT

A novel rose variety of the hybrid tea class characterized by flowers of unique pale pink with darker edging, usually borne singularly on a vigorous upright plant.

1 Drawing Sheet

The present invention relates to a new and distinctive variety of rose plant of the Hybrid Tea class, which was originated by crossing "Agnes Winchel"×unknown seedling.

Among the novel characteristics possessed by the new variety which distinguish it from its parents and all other varieties of which I am aware of are:

(1) A pale pink bloom with slightly darker edges,
(2) A vigorous upright plant,
(3) Exhibition form bloom,
(4) Free bloomer.

Asexual reproduction of the new rose variety by budding, as performed at Wasco, Calif. shows that the aforementioned and all other characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make in a color illustration of this character.

The following is a detailed description of the new variety, with color terminology in accordance with the *Royal Horticultural Society Color Chart.* The terminology used in the colour description herein refers to plate numbers in the aforementioned color chart, e.g. "155A" is plate "155A" of the *Royal Horticultural Society Colour Chart.*

American Rose Society Registration commercial appellation: "Dr. Bob Harvey".

ORAR Appellation: Winbob.

Perentage: Seedling.

*Cross.*—"Agnes Winchel"×unknown seedling. The new rose "Dr Bob Harvey" is unique and may be distinguished from its seed parent "Agnes Winchel" by the following characteristics: (1) "Dr Bob Harvey" is a more virorous growing cultivar that towers over its seed parent. (2) The flower color of "Dr. Bob Harvey" is on the outside edge of the petals a creamy off-white with light pink edges. The inside petals are a soft pink with slightly darker edges. In contrast the seed parent "Agnes Winchel" flower color has a dark pink border on the outside petals that blend downward to a light pink. The inside petals are bordered by deep pink that immediately give way to an almost white petal. (3) The foliage on "Dr. Bob Harvey" is a lighter shade of green in comparison to its seed parent "Agnes Winchel".

Class; Hibrid Tea.

The following observations are made of specimens grown outdoors in Los Angeles County, Calif., in the month October.

FLOWER

Blooming Habit:

A: *Bud.*—(1) Size: Medium with a length of about 7 cm. (2) Form: Pointed with high center. (30 Sepals: Usually very long (about 8 cm, normally extending beyond the bud, no hair, slight serration with no consistant number of appendages, color close to 132C.

(4) Peduncle: 9–10 cm, very strong and erect. Color close to 135C. (5) Color: First color visible when the sepals divide is about 63B. As the petals unfurl the tip of the edges are dark pink close to 63C, the lower edge of the petal fades to a lighter pink close to 62A and the bottom of the petal is a soft white close to 11D.

*Bloom.*—(1) Size: Usually 11.5 cm in diameter. (2) Borne: One to the stem. (3) Form: Long pointed, with a conspicuous neck, very high centers, holds well as flower opens. (4) Petalage: Usually 38–40. (5) Color ; Petal coloration on the upper surface is about 62B with a darker pink border about 62A, at the point of attachment color fades to white about 11D. Petal coloration on the lower surface is a creamy white close to 155B with a thin deep pink border close to 62A.

C: *Petals.*—(1) Texture: Average thickness, excellent substance, holds well in hot weather. (2) Form: Round. (3) Arrangement: Shingle-like (4) Petaloids: None. (5) Fragrance: Damask. (6) Lasting quality; Exceptional for this class, bloom lasts for about fourteen days in the garden, as a cut flower can last for about 6 to 7 days at living room temperature. Petals normally drop completely for an exceptional self-cleaning plant.

REPRODUCTIVE ORGANS

A: Stamen:

(1) *Arrangement.*—Around pistil.
(2) *Number.*—average, close to 100.
(3) *Length.*—About 1.5 cm.
(4) *Filament.*—About 1.25 cm and close to 17B.
(5) *Anthers.*—0.07 cm, color 17C fading to 18A.
(6) *Pollen.*—Normal amount, yellow.

B: Pistil:

(1) *Styles.*—About 1 mm, color close to 6B to 6C, uneven and thin. Number close to 150.
(2) *Stigma.*—Color Close to 6D.
(3) *Ovary.*—Round.
(4) *Average height.*—1.5 cm.

C: Hips: Will accept pollen.

(1) *Shape.*—Globular.

(2) *Color.*—Orange when ripe, color close to 169B.
(3) *Seeds.*—Do not protrude, usually 18–24 per hip.

PLANT

A: Form: Upright, bushy, usually over 4 ft in California climate.
B: Growth; Vigorous.
C: Foliage:
(1) *Size.*—Medium.
(2) *Quantity.—Compound of* 5 to 7 leaflets.
(3) *Color.*—New foliage on upper surface close to 59A, on the lower surface close to 59C. Mature foliage on upper surface is close to 136A, lower surface is dull green close to 138C.
(4) *Shape.*—Oblong — pointed apex.
(5) *Texture.*—Leathery.
(6) *Edge.*—Serrated.
D: Wood:
(1) *New wood.*—Smooth, color close to 143C.
(2) *Mature wood.*—Color close to 133C.
E: Thorns:
(1) *Color.*—Close to 194C. Average amount per cane
F: Resistance to disease:
(1) *Mildew.*—Average.
(2) *Rust.*—Average.
(3) *Black Spot.*—Average.
G: Winter hardiness; Excellent.

I claim:

1. A new and distinctive variety of rose plant of the Hybrid Tea class, substantially as herein shown and described.

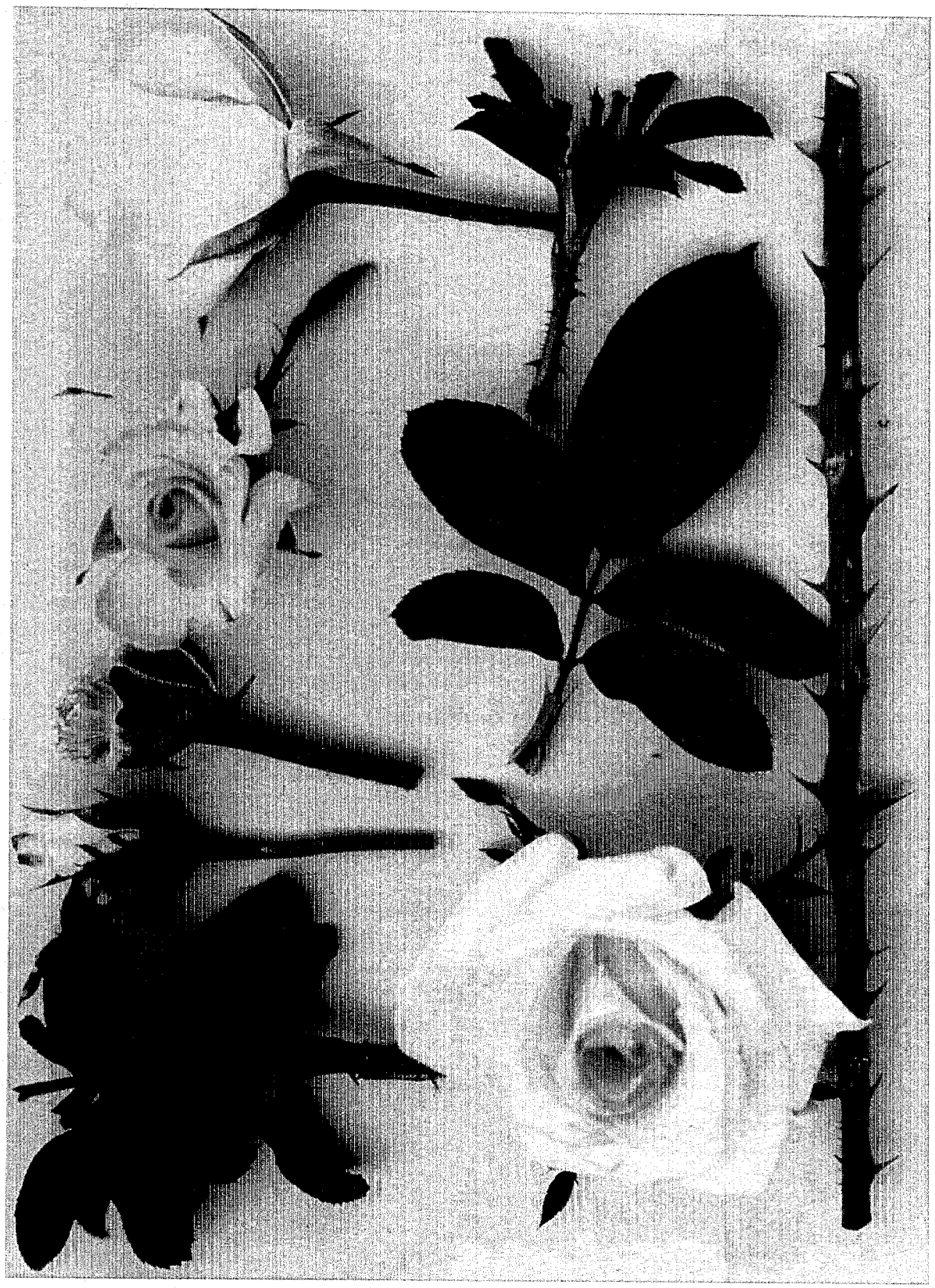

* * * * *